United States Patent
Braga et al.

(10) Patent No.: US 10,016,578 B2
(45) Date of Patent: Jul. 10, 2018

(54) TUNNELING SYSTEM

(71) Applicant: Covidien LP, Mansfield, MA (US)

(72) Inventors: Richard Braga, North Easton, MA (US); Michael Sansoucy, Wrentham, MA (US); Todd Chelak, Westborough, MA (US); Mark Callahan, Medway, MA (US)

(73) Assignee: Covidien LP, Mansfield, MA (US)

( * ) Notice: Subject to any disclaimer, the term of this patent is extended or adjusted under 35 U.S.C. 154(b) by 110 days.

(21) Appl. No.: 15/192,611

(22) Filed: Jun. 24, 2016

(65) Prior Publication Data

US 2016/0303349 A1 Oct. 20, 2016

Related U.S. Application Data

(63) Continuation of application No. 14/184,227, filed on Feb. 19, 2014, now Pat. No. 9,381,038, which is a continuation of application No. 12/206,311, filed on Sep. 8, 2008, now Pat. No. 8,708,897.

(51) Int. Cl.
| | |
|---|---|
| *A61M 25/01* | (2006.01) |
| *A61B 17/32* | (2006.01) |
| *A61B 17/34* | (2006.01) |
| *A61B 17/00* | (2006.01) |

(52) U.S. Cl.
CPC ......... *A61M 25/0194* (2013.01); *A61B 17/32* (2013.01); *A61B 17/3415* (2013.01); *A61M 25/0102* (2013.01); *A61B 2017/00477* (2013.01); *A61B 2017/320056* (2013.01)

(58) Field of Classification Search
CPC ... A61B 17/3415; A61B 2017/320056; A61M 25/0194; A61M 25/0102; A61M 2025/0197
See application file for complete search history.

(56) References Cited

U.S. PATENT DOCUMENTS

| | | | |
|---|---|---|---|
| 1,975,244 | A | 10/1934 | Wiseman |
| 4,299,228 | A | 11/1981 | Peters |
| 4,490,136 | A | 12/1984 | Ekbladh et al. |
| 4,674,496 | A | 6/1987 | Svadjian et al. |
| 4,705,041 | A | 11/1987 | Kim |
| 4,819,694 | A | 4/1989 | Jiang |

(Continued)

FOREIGN PATENT DOCUMENTS

| | | |
|---|---|---|
| CN | 1688352 | 10/2005 |
| JP | 2007523685 | 8/2007 |
| WO | 2005009502 | 2/2005 |

OTHER PUBLICATIONS

"Aspira: Pleural Drainage System", Bard Access Systems, Inc., Salt Lake City, Utah, Instruction Manual dated Oct. 2007, 33 pp.

(Continued)

*Primary Examiner* — Katrina Stransky
(74) *Attorney, Agent, or Firm* — Kenneth Collier; Jessica Kwak Rauckman

(57) ABSTRACT

A tunneling system for use with a catheter includes an elongate tunneling member defining a longitudinal axis along at least a portion of a longitudinal length thereof. The elongate member has a first end and a second end. The tunneling system further includes a connector configured for releasably engaging the second end of the elongate tunneling member to the catheter.

19 Claims, 18 Drawing Sheets

(56) References Cited

U.S. PATENT DOCUMENTS

| | | |
|---|---|---|
| 4,832,687 A | 5/1989 | Smith, III |
| 4,859,111 A | 8/1989 | Borner et al. |
| 5,059,170 A | 10/1991 | Cameron |
| 5,129,891 A | 7/1992 | Young |
| 5,207,643 A | 5/1993 | Davis |
| 5,209,723 A | 5/1993 | Twardowski et al. |
| 5,279,597 A | 1/1994 | Dassa et al. |
| 5,358,506 A | 10/1994 | Green et al. |
| 5,405,320 A | 4/1995 | Twardowski et al. |
| 5,417,511 A | 5/1995 | Warden |
| 5,431,661 A | 7/1995 | Koch |
| 5,470,319 A | 11/1995 | Mayer |
| 5,478,318 A | 12/1995 | Yoon |
| 5,505,714 A | 4/1996 | Dassa et al. |
| 5,509,897 A | 4/1996 | Twardowski et al. |
| 5,562,618 A | 10/1996 | Cai et al. |
| 5,613,945 A | 3/1997 | Cai et al. |
| 5,624,413 A | 4/1997 | Markel et al. |
| 5,632,729 A | 5/1997 | Cai et al. |
| 5,637,102 A | 6/1997 | Tolkoff et al. |
| 5,718,678 A | 2/1998 | Fleming, III |
| 5,743,873 A | 4/1998 | Cai et al. |
| 5,944,732 A | 8/1999 | Raulerson et al. |
| 6,099,519 A | 8/2000 | Olsen et al. |
| 6,113,572 A | 9/2000 | Gailey et al. |
| 6,126,631 A | 10/2000 | Loggie |
| 6,423,053 B1 | 7/2002 | Lee |
| 6,453,185 B1 | 9/2002 | O'Keefe |
| 6,638,242 B2 | 10/2003 | Wilson et al. |
| D498,844 S | 11/2004 | Diamond et al. |
| 6,858,019 B2 | 2/2005 | McGuckin, Jr. et al. |
| 6,872,198 B1 | 3/2005 | Wilson et al. |
| 6,877,927 B2 | 4/2005 | Paulin et al. |
| 6,911,014 B2 | 6/2005 | Wentling et al. |
| 6,916,051 B2 | 7/2005 | Fisher |
| 6,921,396 B1 | 7/2005 | Wilson et al. |
| 6,939,328 B2 | 9/2005 | Raulerson |
| 6,969,381 B2 | 11/2005 | Voorhees |
| 6,979,339 B2 | 12/2005 | Bishop et al. |
| 7,008,395 B1 | 3/2006 | Loggie |
| 7,087,071 B2 | 8/2006 | Nicholas et al. |
| 7,128,734 B1 | 10/2006 | Wilson et al. |
| 7,144,409 B2 | 12/2006 | Aranyi |
| 7,163,531 B2 | 1/2007 | Seese et al. |
| 7,261,708 B2 | 8/2007 | Raulerson |
| 7,300,430 B2 | 11/2007 | Wilson et al. |
| 7,377,915 B2 | 5/2008 | Rasmussen et al. |
| 7,578,803 B2 * | 8/2009 | Rome ............... A61M 25/0097 604/167.03 |
| 8,105,313 B2 | 1/2012 | Schweikert et al. |
| 8,137,316 B2 | 3/2012 | Haarala et al. |
| 8,574,192 B2 | 11/2013 | Haarala et al. |
| 8,708,897 B2 | 4/2014 | Braga et al. |
| 9,248,257 B2 | 2/2016 | Martin et al. |
| 9,381,037 B2 | 7/2016 | Haarala et al. |
| 9,381,038 B2 | 7/2016 | Braga et al. |
| 2004/0034324 A1 | 2/2004 | Seese et al. |
| 2004/0065333 A1 | 4/2004 | Wilson et al. |
| 2004/0158208 A1 | 8/2004 | Hiejima |
| 2004/0167478 A1 | 8/2004 | Mooney et al. |
| 2004/0171997 A1 | 9/2004 | Wilson et al. |
| 2004/0176739 A1 | 9/2004 | Stephens et al. |
| 2004/0230204 A1 | 11/2004 | Wortley et al. |
| 2005/0027282 A1 | 2/2005 | Schweikert et al. |
| 2005/0033268 A1 | 2/2005 | Decaria |
| 2005/0085765 A1 | 4/2005 | Voorhees |
| 2005/0107770 A1 | 5/2005 | Schweikert et al. |
| 2005/0137580 A1 | 6/2005 | Raulerson et al. |
| 2005/0137581 A1 * | 6/2005 | Azar ................... A61M 1/0086 604/542 |
| 2005/0187535 A1 * | 8/2005 | Wilson .............. A61M 25/0069 604/523 |
| 2005/0209581 A1 | 9/2005 | Butts et al. |
| 2005/0209583 A1 | 9/2005 | Powers et al. |
| 2005/0209584 A1 | 9/2005 | Rome |
| 2005/0228364 A1 | 10/2005 | Braga |
| 2005/0256461 A1 | 11/2005 | DiFiore et al. |
| 2005/0261664 A1 | 11/2005 | Rome et al. |
| 2005/0261665 A1 | 11/2005 | Voorhees |
| 2005/0267417 A1 | 12/2005 | Secrest et al. |
| 2006/0009783 A1 | 1/2006 | Rome et al. |
| 2006/0015086 A1 | 1/2006 | Rasmussen et al. |
| 2006/0015130 A1 | 1/2006 | Voorhees, Jr. et al. |
| 2006/0095062 A1 * | 5/2006 | Stephens ............ A61B 17/3415 606/191 |
| 2006/0135949 A1 | 6/2006 | Rome et al. |
| 2006/0224110 A1 | 10/2006 | Scott et al. |
| 2006/0276773 A1 | 12/2006 | Wilson et al. |
| 2007/0016167 A1 | 1/2007 | Smith et al. |
| 2007/0049960 A1 | 3/2007 | Stephens et al. |
| 2007/0060866 A1 | 3/2007 | Raulerson et al. |
| 2007/0078396 A1 | 4/2007 | Feeley et al. |
| 2007/0260221 A1 | 11/2007 | Chesnin |
| 2007/0265597 A1 | 11/2007 | Schweikert et al. |
| 2007/0282274 A1 | 12/2007 | Chesnin |
| 2008/0009832 A1 | 1/2008 | Barron et al. |
| 2008/0027415 A1 | 1/2008 | Isaacson |
| 2008/0086161 A1 * | 4/2008 | Massengale ....... A61B 17/3415 606/190 |
| 2008/0097409 A1 | 4/2008 | Stephens |
| 2008/0214991 A1 | 9/2008 | Haarala et al. |
| 2008/0214992 A1 | 9/2008 | Haarala et al. |
| 2009/0137944 A1 | 5/2009 | Haarala et al. |
| 2010/0063512 A1 | 3/2010 | Braga et al. |
| 2011/0009717 A1 | 1/2011 | Davis et al. |
| 2012/0016266 A1 | 1/2012 | Burkholz |
| 2012/0083794 A1 | 4/2012 | Martin et al. |

OTHER PUBLICATIONS

"Aspira: Pleural Drainage System—Compassionate Treatment", Bard Access Systems, Inc., Product Description Article, 4 pp. (undated).

"Aspira: Pleural Drainage System Product Features", Bard Access Systems, date accessed Apr. 24, 2009, 2 pp.

"Aspira: Pleural Drainage Catheter", Bard Access Systems, 11 pp. (undated).

Prosecution History from U.S. Appl. No. 13/549,938, dated Jan. 23, 2013 through Jul. 26, 2017, 190 pp.

"Luer Adapter," accessed from http://medical-dictionary.thefreedictionary.com/luer+adapter on Aug. 24, 2017, 1 pp.

Prosecution History from U.S. Appl. No. 14/184,227, now U.S. Pat. No. 9,381,038, dated Feb. 20, 2014 through Mar. 9, 2016, 57 pp.

Prosecution History from U.S. Appl. No. 12/206,311, now U.S. Pat. No. 8,708,897, dated Dec. 7, 2010 through Dec. 23, 2013, 179 pp.

Polycath, Polyuethane Central Venous Catheter CVC 100-SoO, CVC I00-6S, CVC 200-60, CVC 200-68, date accessed Apr. 24, 2009, 1 pp.

European Patent Search Report EP 11 18 3344 dated Dec. 21, 2011.

* cited by examiner

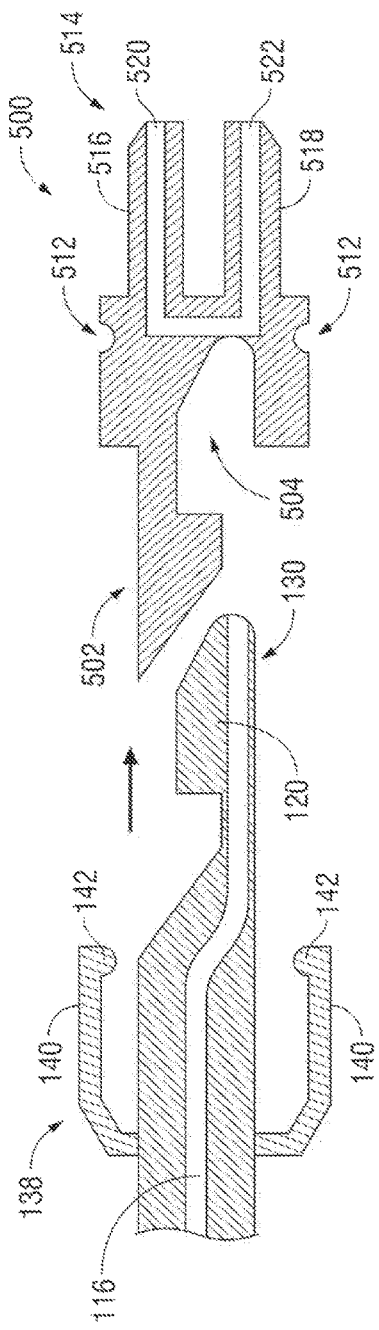
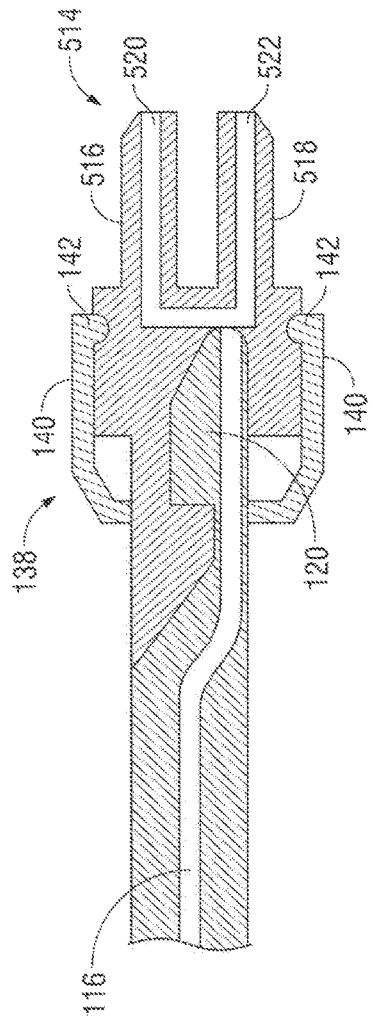
FIG. 3D
FIG. 3E

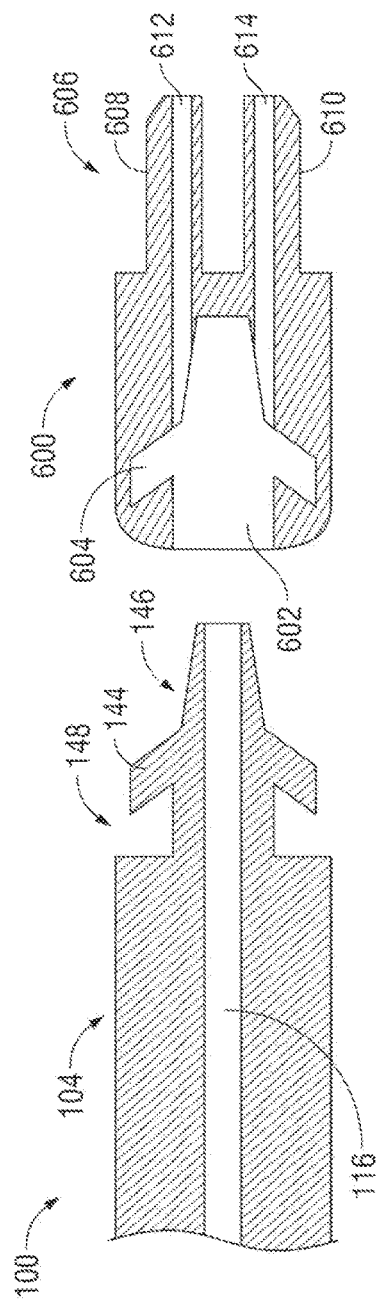
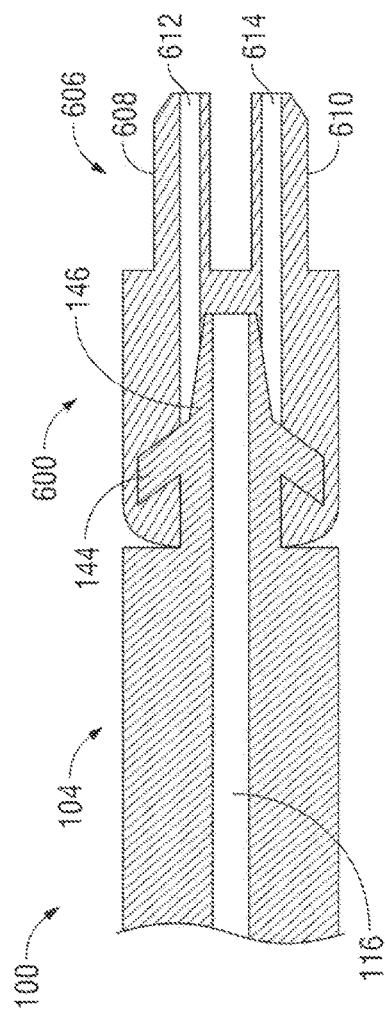
FIG. 4C
FIG. 4D

TUNNELING SYSTEM

CROSS-REFERENCE TO RELATED APPLICATIONS

This application is a continuation of U.S. patent application Ser. No. 14/184,227, filed on Feb. 19, 2014, which is a continuation of U.S. patent application Ser. No. 12/206,311, filed on Sep. 8, 2008, the entire contents of each of which are hereby incorporated by reference.

BACKGROUND

1. Technical Field

The present disclosure relates generally to a tunneling system and, more particularly, relates to a tunneling system connectable to a catheter.

2. Description of the Related Art

Catheters are flexible instruments intended for the withdrawal and introduction of fluids relative to body cavities, ducts, and vessels. Catheters have particular application in hemodialysis procedures where blood is withdrawn from a blood vessel for treatment and subsequently returned to the blood vessel for circulation. Known hemodialysis catheters include multiple lumens, such as dual lumen or triple-lumen catheters, permitting bi-directional fluid flow within the catheter whereby one lumen is dedicated for withdrawal of blood and the other lumen is dedicated for returning treated blood to the vessel. During an exemplary hemodialysis procedure, a multiple lumen catheter is inserted into a body and blood is withdrawn through an arterial lumen of the catheter. The withdrawn blood is directed to a hemodialysis unit which dialyzes, or purifies, the blood to remove waste, and toxins. The dialyzed blood is returned to the subject through a venous lumen of the catheter.

Various devices are employed for the insertion of hemodialysis catheters including, e.g., tunnelers, introduction stylets or the like. A known technique of inserting a catheter includes forming a subcutaneous tunnel between two spaced openings in the skin with the use of a trocar or the like. The catheter end is attached to the trocar or insertion stylet and pulled through the tunnel to expose the catheter which is inserted into, e.g., the jugular vein or other vessel, and routed to the heart. The catheter end must be secured to the trocar in a manner which prevents detachment during passage through the tissue. In addition, the profile of the insertion devices and catheter may need to be minimized for ease of passage through the subcutaneous tissue. Adaptability of a broad range of catheters, tunnelers and sheaths is also a consideration.

SUMMARY

Accordingly, the present disclosure is directed to a tunneling system for use with a catheter. The tunneling system includes an elongate tunneling member defining a longitudinal axis along at least a portion of a longitudinal length thereof and a longitudinal lumen. The elongate member has a first end and a second end. The tunneling system further includes a connector incorporating a tunneling connector segment adapted for releasable coupling to the second end of the elongate tunneling member and a catheter connector segment adapted for coupling with the catheter in secured relation therewith. In one embodiment, the catheter connector segment includes a bifurcated segment incorporating first and second mounting elements extending generally in a longitudinal direction. The first and second mounting elements are dimensioned for reception within respective lumens of the catheter.

Other embodiments of the tunneling system are also disclosed.

BRIEF DESCRIPTION OF THE DRAWINGS

Embodiments of the present disclosure will be better understood with reference to the accompanying drawings, wherein:

FIG. 3D is a side cross-sectional view of the tunneling system shown in FIG. 3A with the elongate tunneling member separated from the connector;

FIG. 3E is a side cross-sectional view of the tunneling system shown in FIG. 3A with the connector attached to the elongate tunneling member;

FIG. 4C is a side cross-sectional view of the tunneling system shown in FIG. 4A with the elongate tunneling member separated from the connector;

FIG. 4D is a side cross-sectional view of the tunneling system shown in FIG. 4A with the connector coupled to the elongate tunneling member;

DETAILED DESCRIPTION OF THE EMBODIMENTS

The exemplary embodiments of the present disclosure are directed to a tunneling system incorporating a connector adapted for interconnecting an elongate tunneling member and a catheter. The tunneling system of the present disclosure may have various medical applications. During a hemodialysis catheter implantation procedure, the tunneling system creates or enlarges a subcutaneous tunnel within a subject and positions a catheter in the target site. It is envisioned, however, that the presently disclosed tunneling system may be employed in any other suitable procedure. For instance, the tunneling system of the present disclosure may be utilized for subcutaneously implanting vascular devices such as stents, vascular grafts, or the like, inside a subject's body.

In the discussion that follows, the term "clinician" refers to a doctor, a nurse, or any other care provider and may include support personnel. The term "proximal" refers to the portion of a structure that is closer to a clinician, whereas the term "distal" refers to the portion that is farther from the clinician.

Figure 1A:
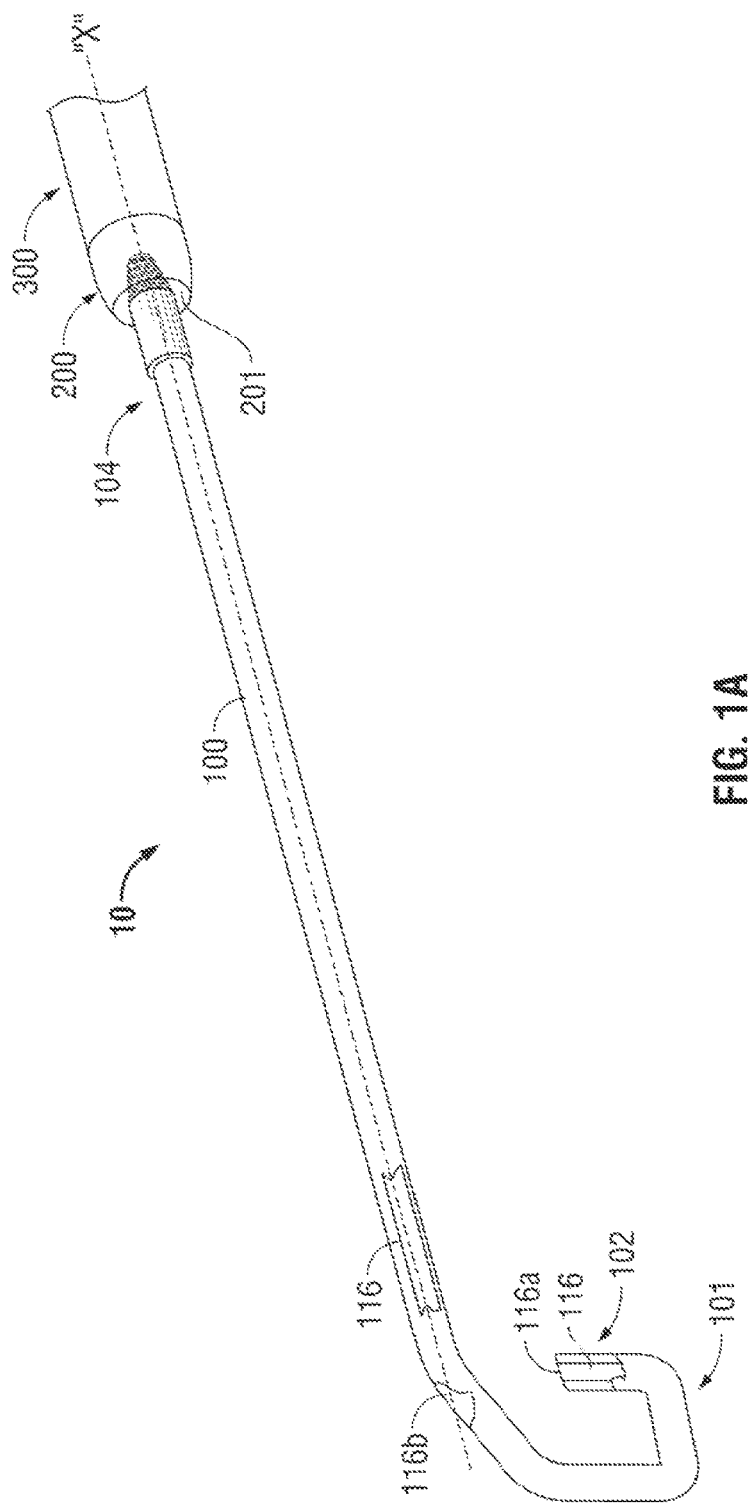
FIG. 1A is a perspective view of a tunneling system illustrating an elongate tunneling member and a connector for releasably coupling a catheter.
Figure 1B:
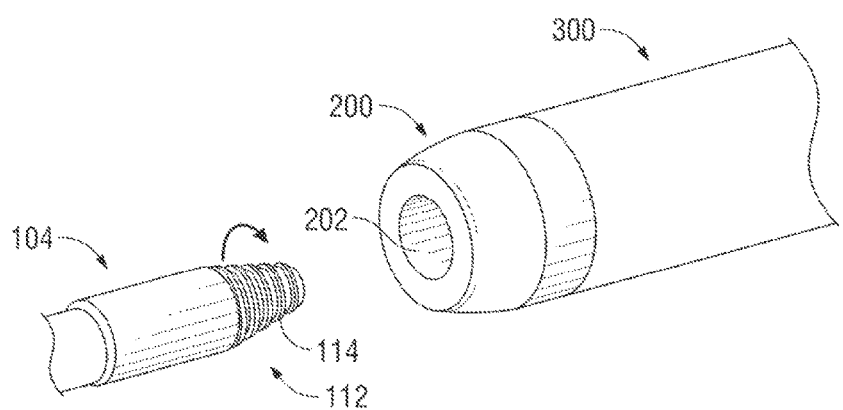
FIG. 1B is an enlarged perspective view of the tunneling system shown in FIG. 1A with an elongate tunneling member having a threaded tip and a connector attached to a catheter.
Figure 1C:
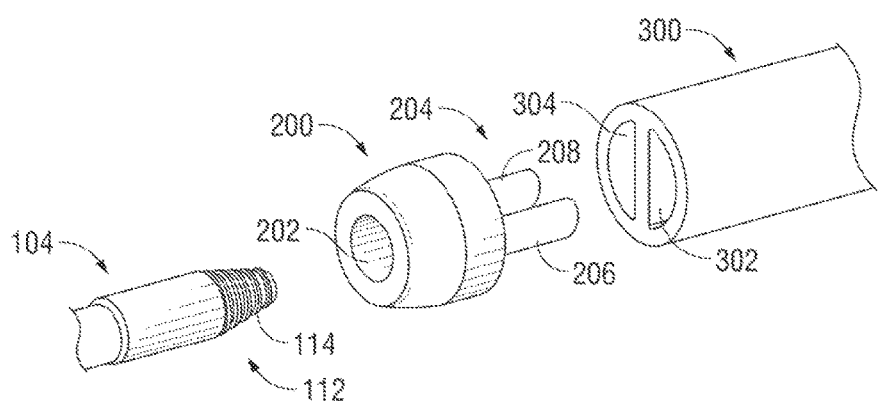
FIG. 1C is an enlarged perspective view of the tunneling system shown in FIG. 1B with the connector released from the catheter.
Figure 1D:
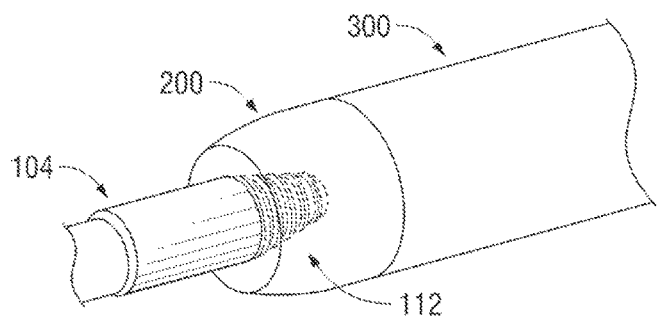
FIG. 1D is an enlarged perspective view of the tunneling system shown in FIG. 1B with the connector mounted to the elongate tunneling member and the catheter.
Figure 1E:
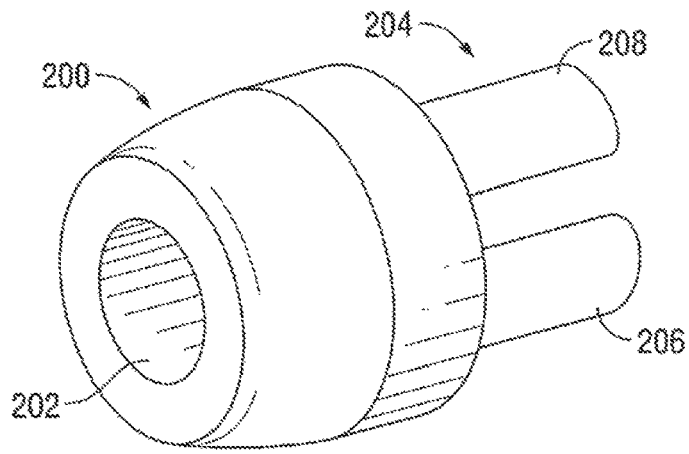
FIG. 1E is an enlarged perspective view of the connector shown in FIG. 1B.

Referring now in detail to the drawings where like reference numerals identify similar or like components throughout the several views, FIG. 1A generally illustrates the tunneling system 10 of the present disclosure. In brief, tunneling system 10 includes elongate tunneling member 100 releasably coupled to connector 200. Connector 200 is capable of engaging catheter 300 in secured relation. During operation, elongate tunneling member 100 establishes and/or enlarges a subcutaneous tunnel within a subject. The clinician then attaches elongate tunneling member 100 to catheter 300 by connector 200. The secured interconnection between elongate tunneling member 100, connector 200, and catheter 300 allows the clinician to maneuver the catheter 300 within the subcutaneous tunnel by directing the movement of the elongate tunneling member 100. Thus, tunneling system 10 facilitates the placement of catheter 300 inside a subject at desired predetermined locations. A clinician may position catheter 300 in the target site with tunneling system 10 by performing the ante grade and reverse tunneling procedures described in U.S. Pat. No. 5,509,897 to Twardowski. The entire contents of U.S. Pat. No. 5,509,897 are hereby incorporated by reference herein.

Elongate tunneling member 100 of tunneling system 10 defines a longitudinal axis "X" along at least a portion of a longitudinal length thereof and has first end 102 and second end 104. First end 102 of elongate tunneling member 100 is adapted for grasping engagement and handling by a clinician. Second end 104 of elongate tunneling member 100 is configured for connection to connector 200.

Figure 1F:
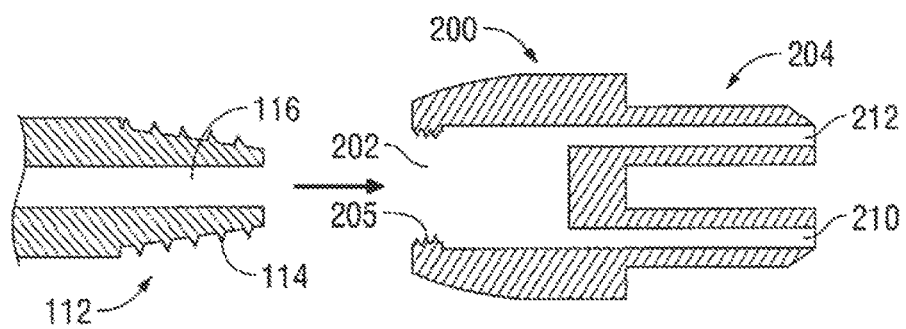
FIG. 1F is a side cross-sectional view of the tunneling system shown in FIG. 1B with the elongate tunneling member separated from the connector.
Figure 1G:
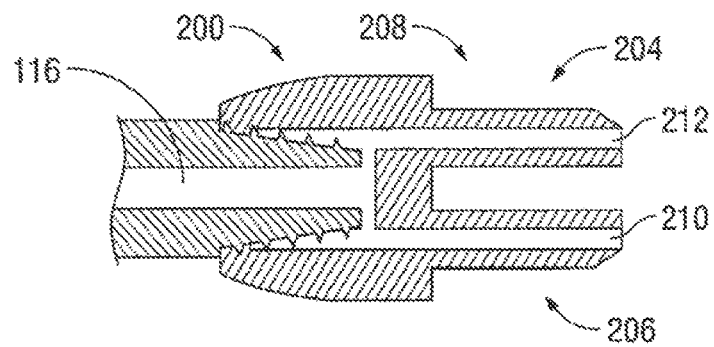
FIG. 1G is a side cross-sectional view of the tunneling system shown in FIG. 1B with the elongate tunneling member coupled to the connector.
Figure 1H:
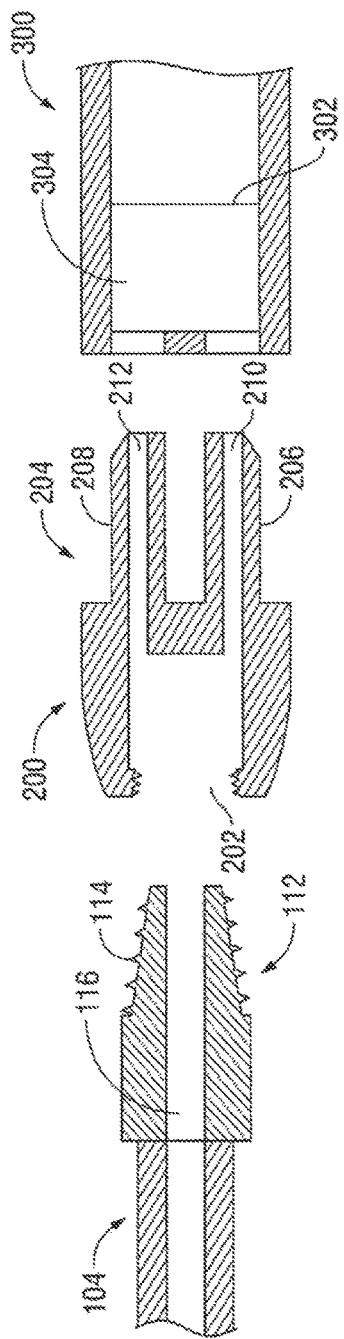
FIG. 1H is a side cross-sectional view of the elongate tunneling member, the connector, and the catheter shown in FIG. 1B.
Figure 1I:
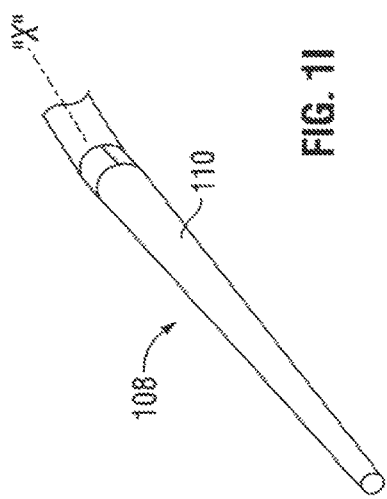
FIG. 1I is an enlarged perspective view of an alternate embodiment of the tunneling system illustrating an end of the elongate tunneling member configured for passage through tissue.
Figure 2A:
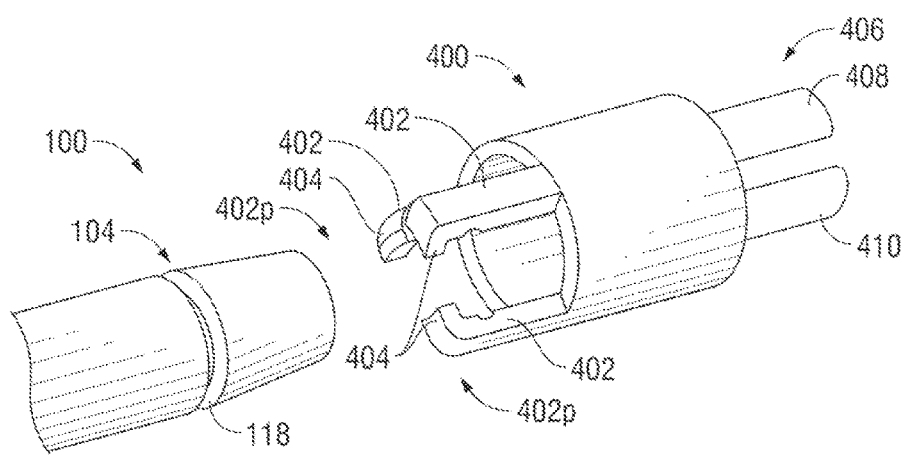
FIG. 2A is an enlarged perspective view of an alternative embodiment of the tunneling system incorporating a connector with a plurality of resilient locking members.
Figure 2B:
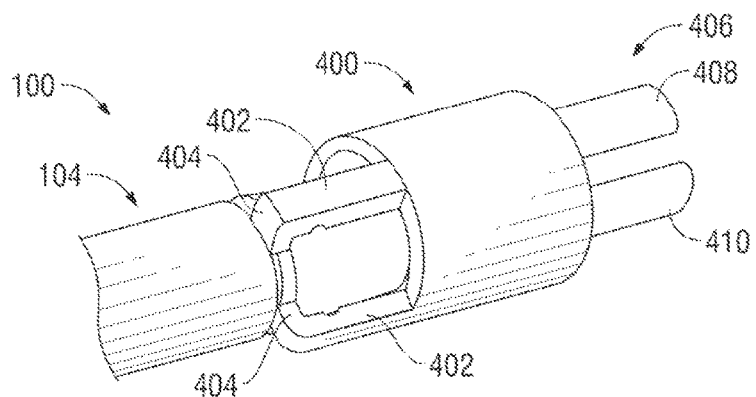
FIG. 2B is an enlarged perspective view of the tunneling system shown in FIG. 2A with the connector secured to the elongate tunneling member.
Figure 2C:
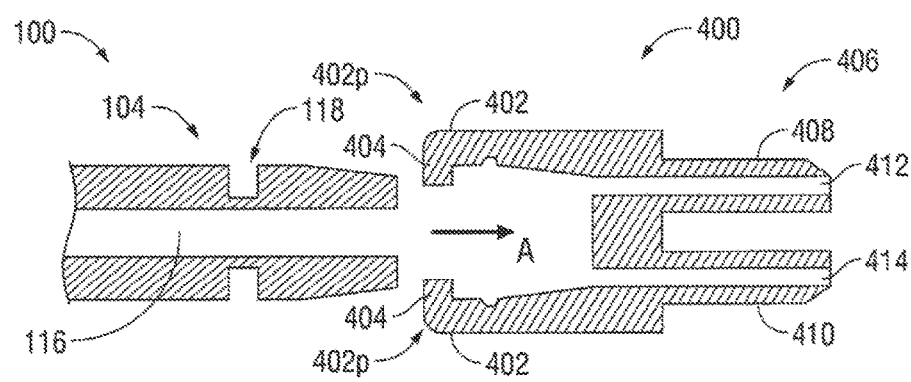
FIG. 2C is a side cross-sectional view of the tunneling system shown in FIG. 2A with the connector separated from the elongate tunneling member.
Figure 2D:
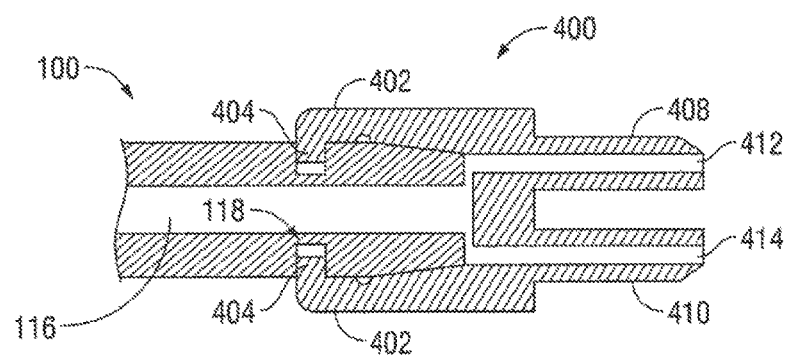
FIG. 2D is a side cross-sectional view of the tunneling system shown in FIG. 2A with the connector attached to the elongate tunneling member.
Figure 3A:
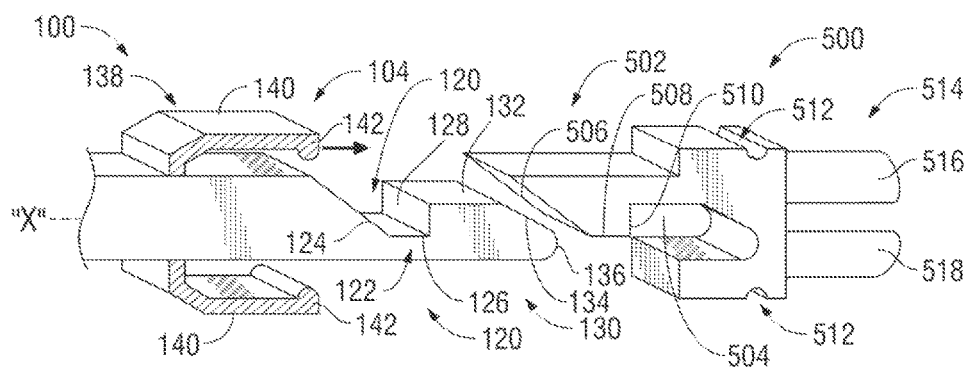
FIG. 3A is an enlarged perspective view of an alternate embodiment of the tunneling system incorporating an elongate tunneling member with a plurality of resilient locking members and a first interlocking snap head and a connector with a second interlocking head.
Figure 3B:
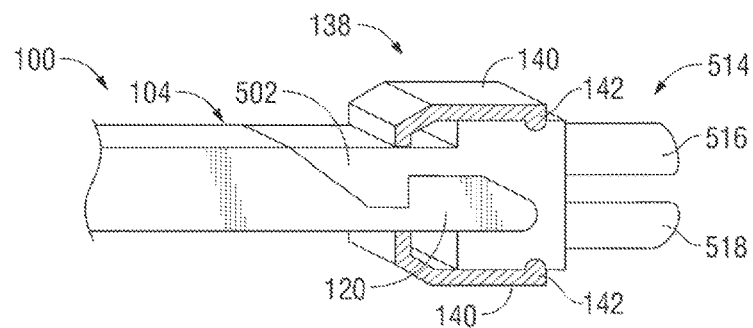
FIG. 3B is an enlarged perspective view of the tunneling system shown in FIG. 3A with the elongate tunneling member attached to the connector.
Figure 3C:
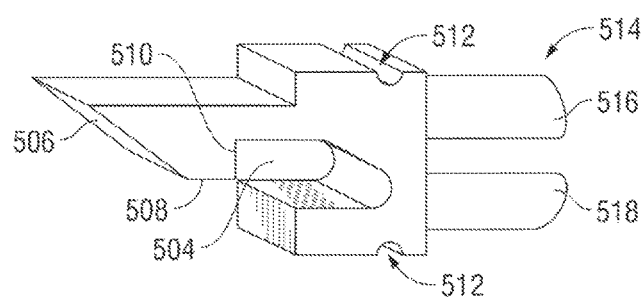
FIG. 3C is an enlarged perspective view of the connector shown in FIG. 3A.
Figure 4A:
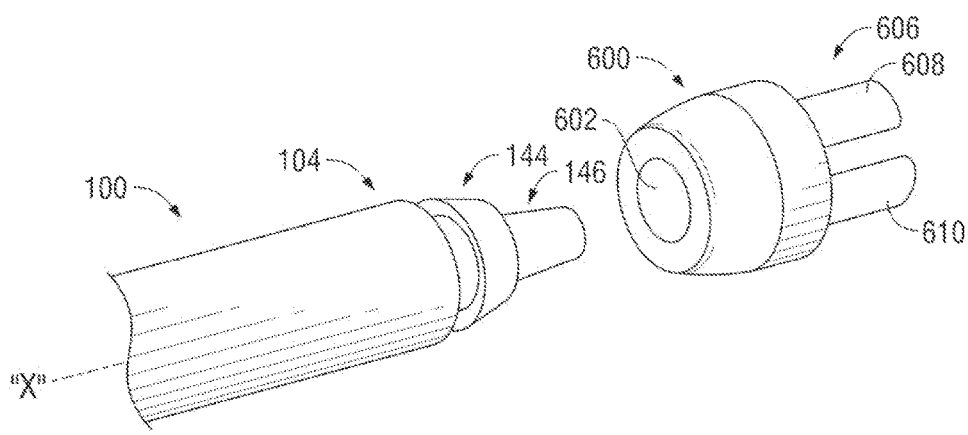
FIG. 4A is an enlarged perspective view of an alternate embodiment of the tunneling system incorporating an elongate tunneling member with a radially depending barb.
Figure 4B:
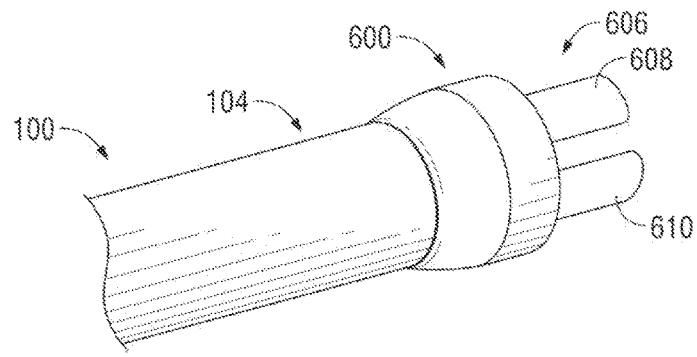
FIG. 4B is an enlarged perspective view of the tunneling system shown in FIG. 4A with the elongate tunneling member coupled to the connector.

In an alternate embodiment, elongate tunneling member 100 includes first end 108 configured for passage through tissue to create or enlarge a subcutaneous tunnel within a subject, as shown in FIG. 1I. First end 108 includes offset segment 110 dimensioned to facilitate passage through the subcutaneous tunnel. Offset segment 110 may incorporate any angular or arcuate arrangement suitable to facilitate insertion and/or passage through the tissue when elongate tunneling member 100 is manipulated by the clinician. In one embodiment, offset segment 110 is obliquely arranged with respect to the longitudinal axis "X" of elongate tunneling member 100 at a relatively small angle. Other arrangement and angular relationships of offset segment 110 are also envisioned.

As seen in FIGS. 1A-1H, an embodiment of the tunneling system 10 includes elongate tunneling member 100 with tapered tip 112 (FIG. 1B) positioned at second end 104. Elongate tunneling member 100 may define longitudinal lumen 116 (FIG. 1A) extending therethrough. Lumen 116 may extend through first end 201 of connector 200. FIG. 1A illustrates longitudinal lumen 116 (in phantom) extending through elongate tunneling member 100. Lumen 116 may terminate at port 116a which is defined in handle 101. Port 116a may be connected to a fluid source by conventional means. Alternatively, longitudinal lumen 116 may terminate at port 116b which is in alignment with longitudinal axis x and forward of handle 101. Tapered tip 112 of elongate tunneling member 100 defines thread 114 and is dimensioned for insertion within connector 200.

Connector 200 includes bifurcated segment 204 (FIG. 1B) and defines longitudinal lumen 202 adapted for receiving the tapered tip 112. The internal surfaces of connector 200 defining longitudinal lumen 202 may form an inner thread 205 (FIG. 1F) adapted to engage the thread 114 of the second end 104 of the elongate tunneling member 100. In the alternative, in the absence of an inner thread of connector 200, thread 114 may be sharp to "bite into" internal surfaces of connector 200 defining longitudinal lumen 202. In another alternative, longitudinal lumen 202 of connector 200 may define a female luer taper adapted to receive a corresponding male luer taper of tapered tip 112 of tunneling member 100.

Bifurcated segment 204 may include a pair of mounting elements 206, 208 each adapted for insertion in respective lumens 302, 304 of catheter 300. Mounting elements 206, 208 extend longitudinally in a distal direction and, as illustrated in FIGS. 1F-1H, each may define corresponding longitudinal lumens 210, 212 extending therethrough. Both longitudinal lumens 210, 212 of respective mounting elements 206, 208 are in fluid communication with the longitudinal lumen 116 of the elongate tunneling member 100 when the tapered tip 112 is inserted into the connector 200, as depicted in FIG. 1G. In one embodiment, connector 200 includes a female luer taper for fluidly connecting elongate tunneling member 100 to catheter 300.

To maneuver the catheter 300 with the tunneling system 10, the elongate tunneling member 100 (FIG. 1A) is connected to catheter 300 by inserting tapered tip 112 into longitudinal lumen 202 of connector 200, and, optionally, rotating the tunneling member 100. During this process, thread 114 of tapered tip 112 engages the internal surfaces defining longitudinal lumen 202 or thread 205 if present, thereby securing elongate tunneling member 100 to connector 200. Connector 200 is coupled to catheter 300 by positioning mounting elements 210, 210 of bifurcated segment 204 into a respective longitudinal lumen 302, 304 of catheter 300 to attach connector 200 to the catheter 300. Alternatively, connector 200 may be secured or glued to the catheter 300. Once the catheter 300 and the elongate tunneling member 100 are attached to the connector 200, longitudinal lumens 302, 304 are in fluid communication with the longitudinal lumen 116 of elongate tunneling member 100. This fluid connection may provide flushing and/or aspiration capabilities through longitudinal lumens 302, 304 of catheter 300 during the catheter insertion procedure. Once elongate tunneling member 100 and catheter 300 are coupled, the clinician may maneuver the catheter 300 through the manipulation of elongate tunneling member 100.

FIGS. 2A-2D illustrate an alternate embodiment of the tunneling system 10 incorporating a connector 400 with a plurality of lock members 402. Although the drawings illustrate a connector 400 including three lock members 402, connector 400 may have one or more lock members 402. Each lock member 402 includes locking detent 404. Locking detent 404 is configured to be received within locking member 118 of elongate tunneling member 100, thereby securing connector 400 to the elongate tunneling member 100. In exemplary embodiments, locking members 118 may be one or more annular grooves, thru-holes, notches, cut outs, or the like. In the embodiment depicted in FIGS. 2A-2D, locking member 118 is an annular groove. Annular groove 118 is defined along the circumference of second end 104 of elongate tunneling member 100 and is configured to receive the locking detents 404. In the alternative, annular grooves 118 may be replaced with holes or the like. In addition to locking detents 404, connector 400 includes a bifurcated segment 406 attachable to the catheter 300. Bifurcated segment 406 incorporates first and second mounting element 408, 410 adapted for reception within respective longitudinal lumens 302, 304 of catheter 300. Each mounting element 408, 410 may define respective longitudinal lumens 412, 414 extending along the length thereof. When connector 400 is secured to elongate tunneling member 100, longitudinal lumens 412, 414 are in fluid communication with longitudinal lumen 116 of elongate tunneling member 100. Thus, longitudinal lumens 412, 414 of mounting elements 408, 410 define a channel fluidly connecting longitudinal lumens 302, 304 of catheter 300 to longitudinal lumen 116 of the elongate tunneling member 100 when connector 400 is coupled to catheter 300 and elongate tunneling member 100.

During operation, the clinician attaches connector 400 to elongate tunneling member 100 by positioning locking detents 404 inside annular groove 118 of elongate tunneling member 100. The clinician merely has to advance the elongate tunneling member 100 toward connector 400 in the direction indicated by arrow "A" until the locking detents 404 of each lock member 402 snaps into annular groove 118, thereby securing elongate tunneling member 100 to connector 400. Lock members 402 and associated locking detents 404 may be sufficiently resilient to flex outwardly during initial placement over elongate member 100 whereby upon approaching annular groove 118, the lock members 402 and locking detents 404 move or return toward the initial position with the locking detents 404 secured within annular groove 118. Connector 400 is then joined to the catheter 300 by inserting mounting element 408, 410 into the respective longitudinal lumens 302, 304 of catheter 300.

With reference to FIGS. 3A-3E, another embodiment of the tunneling system 10 includes connector 500 and elongate tunneling member 100 each containing interlocking snap heads 502, 120 respectively. Interlocking snap head 120 defines recess 122 for receiving interlocking snap head 120, and is located at second end 104 of elongate tunneling member 100. Recess 122 includes angled surface 124 defining an angle with respect to the longitudinal axis "X," engaging surface 126 that is substantially parallel to the longitudinal axis "X," and abutment surface 128 that is substantially perpendicular to the longitudinal axis "X." Interlocking snap head 120 additionally incorporates locking tip 130 defining abutting surface 132 that is substantially parallel to the longitudinal axis "X," a slanted surface 134 angled with respect to the longitudinal axis "X," and blunt end 136 for facilitating insertion of second end 104 of elongate tunneling member 100 into connector 500.

Elongate member 100 also includes snap fit member 138 slidably positioned about second longitudinal end 104. Snap fit member 138 contains a pair of arms 140 disposed in opposed relation to each other. Each arm 140 incorporates locking detent 142 for connecting the elongate tunneling member 100 to connector 500.

Interlocking snap head 502 is adapted to engage interlocking snap head 120 of elongate tunneling member 100. Interlocking snap head 502 defines opening 504 dimensioned to receive locking tip 130 of interlocking snap head 120, inclined surface 506 delineating an angle that is complementary to the angle defined by angled surface 124, engaging surface 508 adapted for reception within recess 122, and perpendicular surface 510 configured to press against abutment surface 128 when interlocking snap heads 120, 502 are connected to each other. Connector 500 further includes longitudinal grooves 512 for receiving locking detents 142 of snap fit member 138 and bifurcated segment 514 connectable to the catheter 300. Bifurcated segment 514 incorporates first and second mounting elements 516, 518 adapted for insertion within respective longitudinal lumens 302, 304 of catheter 300. First and second mounting elements 516, 518 include respective longitudinal lumens 520, 522 as illustrated in FIGS. 3D and 3E. When elongate tunneling member 100 is connected to connector 500, longitudinal lumens 520, 522 are in fluid communication with longitudinal lumen 116 of elongate tunneling member 100.

During operation, the clinician advances second end 104 of elongate tunneling member 100 toward connector 500 until interlocking snap heads 120, 502 engages each other. With interlocking snap heads 120, 502 in engaged relation, opening 504 partially encloses locking tip 130 and recess 122 retains engaging surface 508 and perpendicular surface 510, and inclined surface 506 abuts angled surface 124. After inserting locking tip 130 into opening 504, the clinician slides snap fit member 138 toward connector 500 until locking detents 142 snap into longitudinal grooves 512. In this position, snap fit member 138 encompasses snap fit heads 502 and 120. The clinician then inserts mounting elements 516, 518 into the respective longitudinal lumens 302, 304 of catheter 300. After properly securing connector 500 to elongate tunneling member 100 and catheter 300, the clinician may control the movement of catheter 300 through cooperative movement of elongate tunneling member 100.

FIGS. 4A-4D illustrate an embodiment of tunneling system 10 including connector 600 and elongate tunneling member 100 with barb 144 depending radially with respect to the longitudinal axis "X." Barb 144 is located on the second end 104 of elongate tunneling member 100 and defines an angle relative to longitudinal axis "X." Second end 104 additionally includes luer fitting 146 located distally with respect to barb 144 and recess 148 positioned proximally with respect to the barb 144. Luer fitting 146 is configured for reception within opening 602 of connector 600.

Opening 602 of connector 600 is dimensioned to receive luer fitting 146 and defines annular indentation 604 adapted to receive barb 144. Connector 600, which may be made of a flexible material, further includes bifurcated segment 606 for connecting the connector 600 to the catheter 300. Specifically, bifurcated segment 606 incorporates first and second mounting elements 608, 610 adapted for reception within respective longitudinal lumens 302, 304 of catheter 300. Mounting element 608, 610 extends longitudinally in and defines respective longitudinal lumens 612, 614 therethrough. When the elongate tunneling member 100 is operatively coupled to connector 600, luer fitting 146 fluidly connects the longitudinal lumen 116 of elongate member 100 to the longitudinal lumens 612, 614 of mounting elements 608, 610.

During operation, the clinician advances the second end 104 of elongate tunneling member 100 to the connector 600 and inserts luer fitting 146 into opening 602. While advancing second longitudinal end 104 of elongate tunneling member 100, connector 600 slightly expands to allow passage of barb 144. The clinician continues to advance second longitudinal end 104 until annular indentation 604 receives and locks barb 144 therein. Thereafter, the connector 600 is attached to catheter 300 by inserting mounting elements 608, 610 into the respective longitudinal lumens 302, 304 of catheter 300. Once connector 600 is operatively coupled to catheter 300 and elongate tunneling member 100, the clinician may manipulate the movement of catheter 300 through elongate tunneling member 100.

Figure 5A:
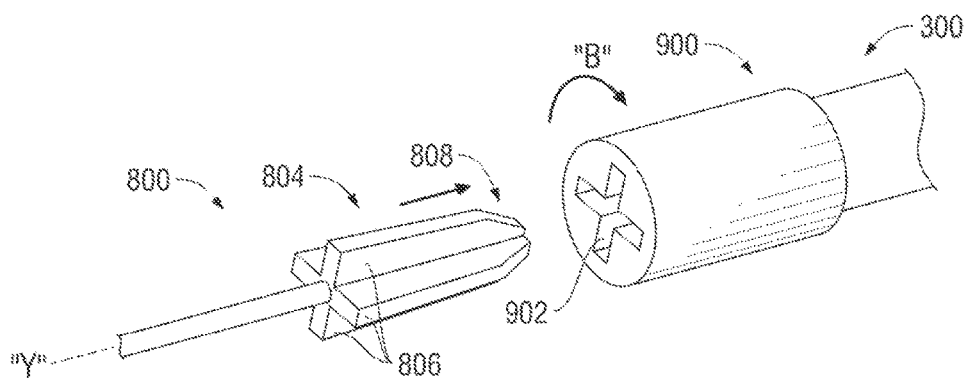
FIG. 5A is an enlarged perspective view of an alternative embodiment of the tunneling system incorporating an elongate tunneling member with a plurality of ribs having a tapered profile.
Figure 5B:
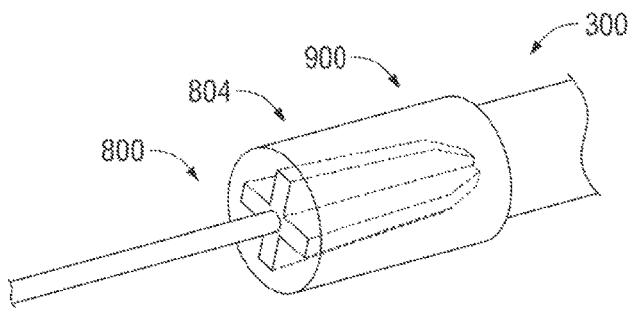
FIG. 5B is an enlarged perspective view of the tunneling system illustrated in FIG. 5A with the elongate tunneling member attached to the connector.
Figure 5C:
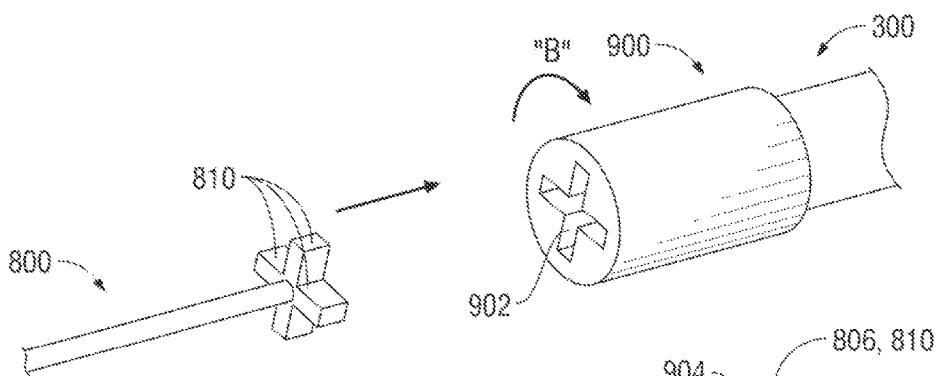
FIG. 5C is an enlarged perspective view of an alternate embodiment of the tunneling system incorporating an elongate tunneling member with a plurality of ribs without a tapered profile.

FIGS. 5A and 5B depict an embodiment of the tunneling system 10. This embodiment includes elongate member 800 incorporating a plurality of ribs 806 and connector 900 defining slot 902 adapted to receive the ribs 806. Elongate tunneling member 800 defines longitudinal axis "Y" along at least a portion of its length. Ribs 806 are located at second longitudinal end 804 of elongate tunneling member 800 and extend radially with respect to longitudinal axis "Y." In this embodiment, elongate tunneling member 800 incorporates four ribs 806; however, elongate tunneling member 800 may contain more or fewer ribs 806 insofar as the ribs 806 are capable of connecting elongate tunneling member 100 to connector 900. Each rib 806 has an elongate structure and defining a cuboid shape. Together, four ribs 806 define a cross-shaped cross-section and tapered tip 808. Tapered tip 808 facilitates insertion of ribs 806 through slot 902 of connector 900. Alternatively, elongate tunneling member 800 may contain ribs 810 lacking a tapered tip, as shown in FIG. 5C.

Connector 900 defines slots 902 dimensioned to receive ribs 806 or ribs 810. Slots 902 allow passage of ribs 806 to an internal cavity 904 of connector 900. The internal cavity 904 of connector 900 may be cylindrical or annular in configuration to accommodate ribs 806. Connector 900 is mounted to the catheter 300 by any suitable means such as crimping, adhesives, etc. In operation, the clinician may rotate connector 900 about the longitudinal axis "Y" to change the angular position of slot 902.

During use, the clinician moves the elongate tunneling member 800 toward connector 900 and inserts ribs 806 or ribs 810 through slot 902 until the entire lengths of the ribs 806 are located inside the internal cavity 904 of connector 900. After positioning ribs 806 inside the internal cavity 904 of connector 900, the clinician rotates connector 900 in the direction indicated by the arrow "B." As the connector 900 rotates about longitudinal axis "Y," slot 902 changes position and precludes ribs 806, 810 from exiting the internal cavity 904 of connector 900.

Figure 5D:
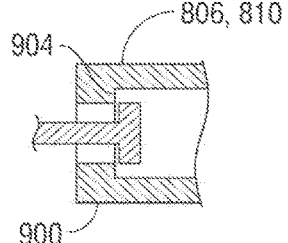
FIG. 5D is an enlarged cross-sectional view illustrating the ribs of the elongate tunneling member of FIGS. 5A-5C secured within an internal cavity of the connector.

FIG. 5D illustrates ribs 806, 810 secured within internal cavity 904 of connector 900 subsequent to relative angular movement of connector 900 and tunneling member 800. Once elongate tunneling member 800 is secured to catheter 300 through connector 900, the clinician may maneuver catheter 300 through manipulation of elongate tunneling member 800.

Figure 6A:
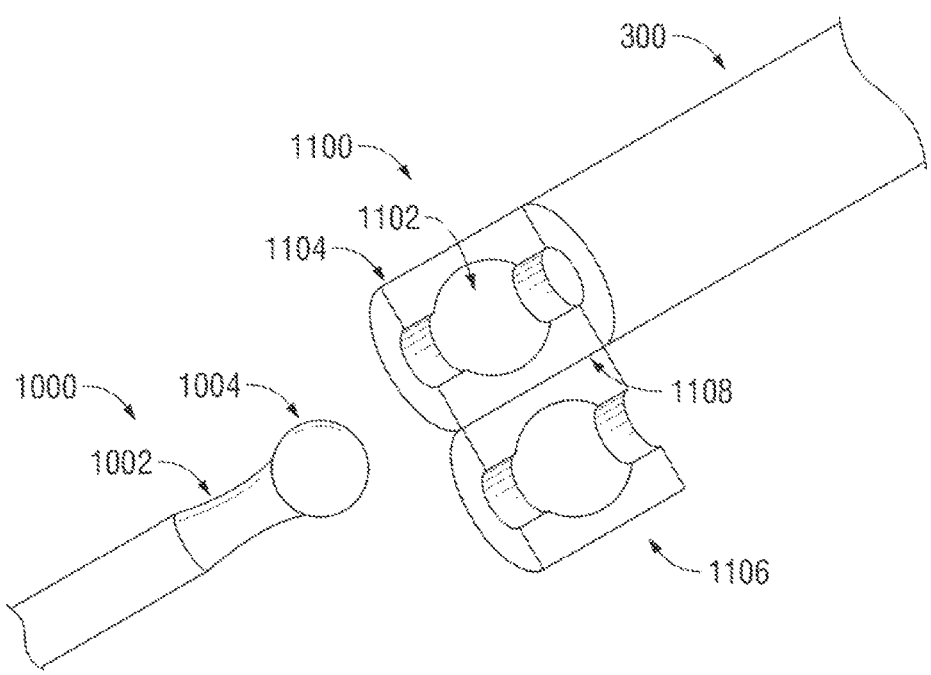
FIG. 6A is an enlarged perspective view of an alternate embodiment of the tunneling system incorporating an elongate tunneling member with a ball and a connector with a socket.
Figure 6B:
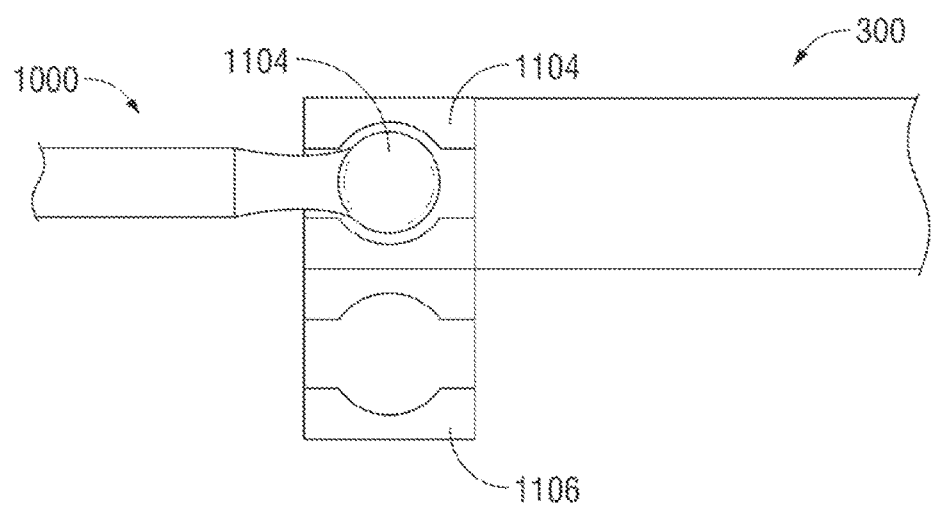
FIG. 6B is top plan view of the tunneling system shown in FIG. 6A with the ball positioned in the socket and the socket in an open position.
Figure 6C:
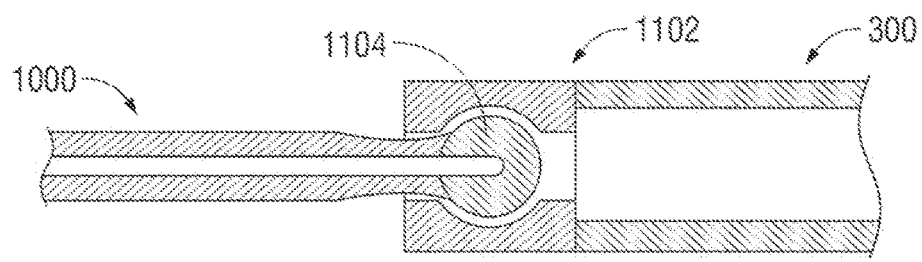
FIG. 6C is a side cross-sectional view of the tunneling system illustrated in FIG. 6A with the elongate tunneling member attached to the connector.

FIGS. 6A-6C show an alternative embodiment of tunneling system 10 incorporating elongate tunneling member 1000 with ball 1004 and a connector 1100 with socket 1102 for receiving the ball 1004. Ball 1004 is located on second end 1002 of elongate tunneling member 1000 and is dimensioned for reception within socket 1102. Connector 1100 is attached to catheter 300 by any suitable means such as crimping, adhesives, etc. Socket 1102 of connector 1100 is formed by first and second segments 1104, 1106. A hinge 1108, or any other suitable apparatus, pivotally connects first and second segments 1104, 1106 to each other. Together, first and second segments 1104, 1106 define socket 1102. During use, first and second segments 1104 move between an open position, as shown in FIG. 6A, and a closed position, as depicted in FIG. 6C.

In operation, the clinician attaches elongate tunneling member 1000 to connector 1100 by positioning ball 1004 inside socket 1102 as depicted in FIG. 6B. To lock ball 1104 inside socket 1102, the clinician then pivots second segment 1106 of connector 1100 to the closed position, as shown in FIG. 6C. The secured interconnection of ball 1104 and socket 1102 enables the clinician to maneuver the catheter 300 through cooperative movement of elongate member 1000. Moreover, the clinician may articulate elongate tunneling member 1000 while moving catheter 300.

Figure 7A:
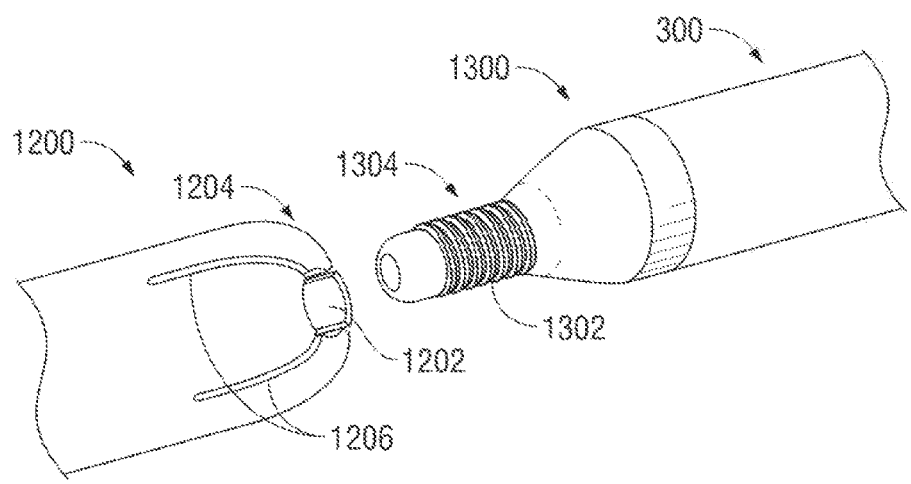
FIG. 7A is an enlarged perspective view of an alternative embodiment of the tunneling system incorporating a connector with a threaded tip.
Figure 7B:
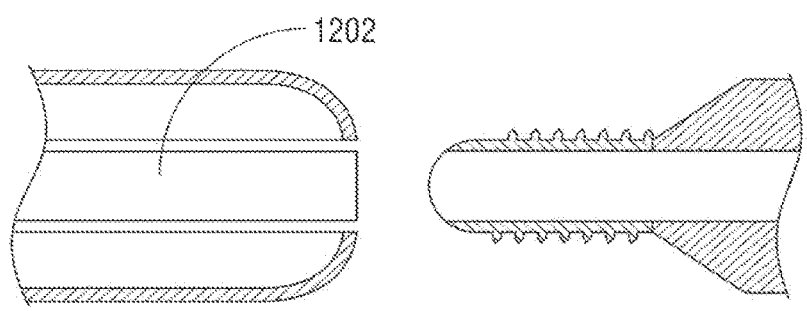
FIG. 7B is a side cross-sectional view of the tunneling system shown in FIG. 7B.

FIGS. 7A and 7B illustrate an alternative embodiment of the tunneling system 10 including elongate tunneling member 1200 and connector 1300 with external thread 1302 formed thereabout. Elongate tunneling member 1200 defines a longitudinal lumen 1202 extending therethrough. Longitudinal lumen 1202 is dimensioned to receive elongate segment 1304 of the connector 1300. Elongate tunneling member 1200 further defines a plurality of slits 1206 at a second longitudinal end 1206 thereof. Slits 1206 allow the second longitudinal end 1204 to slightly expand while a clinician inserts elongate segment 1304 of connector 1300 through longitudinal lumen 1202.

Connector 1300 is operatively attached to catheter 300 by any suitable means such as adhesives and includes an elongate segment 1304 dimensioned for reception within the longitudinal lumen 1202 of elongate tunneling member 1200. Elongate segment 1204 has a thread 1302 formed around its circumference. During use, thread 1302 engages the internal surfaces of elongate tunneling member 1200, thereby securing connector 1300 to elongate tunneling member 1200.

In operation, the clinician inserts the elongate segment 1304 of connector 1300 into longitudinal lumen 1202 of elongate tunneling member 1200. As the elongate segment 1304 enters longitudinal lumen 1202, thread 1302 engages the internal surfaces of elongate tunneling member 1200 and secures connector 1300 to elongate tunneling member 1200. To facilitate engagement of thread 1302 with the internal surfaces of the elongate tunneling member 1200, the clinician may rotate the connector 1300 while inserting elongate segment 1304 into longitudinal lumen 1202. Once the clinician has properly secured connector 1300 to elongate tunneling member 1200, catheter 300 may be maneuvered through the cooperative movement of elongate tunneling member 1200.

Figure 8:
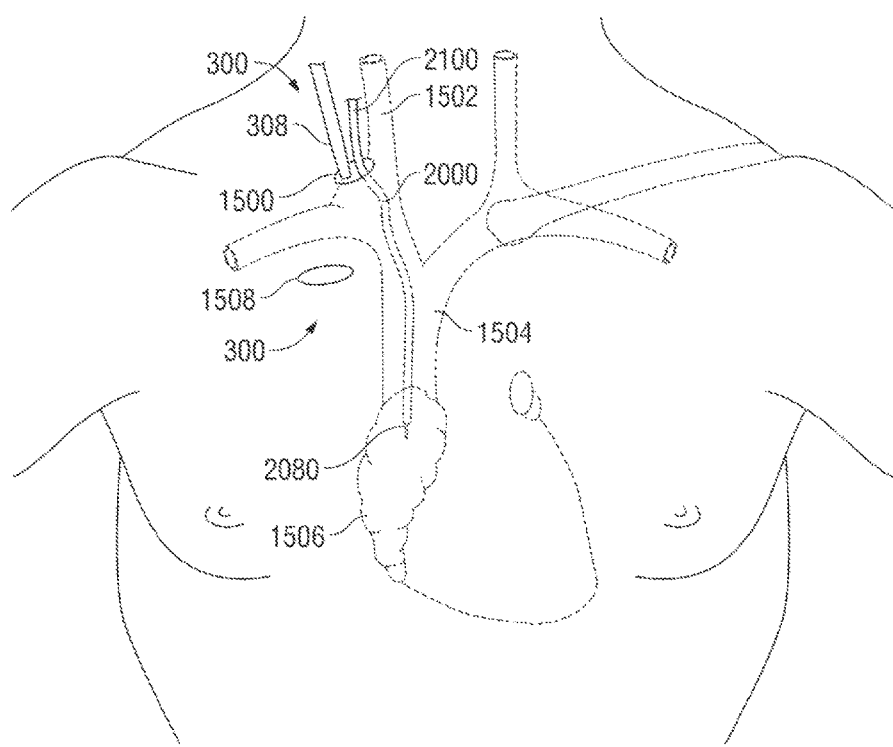
FIGS. 8-9 are views of a chest area of a subject illustrating the steps of a reverse tunneling procedure.

As discussed above, any of the embodiments of the presently disclosed tunneling system 10 may be utilized during a reverse tunneling procedure. In this procedure, tunneling system 10 creates or enlarges a subcutaneous tunnel for deploying any suitable catheter inside the right atrium of the heart through, e.g., the right jugular vein. As appreciated, the catheter 2000 may be implanted in the right atrium via the left jugular vein, the right atrium through the right subclavian vein, the right atrium through the left subclavian vein, or implanted in the femoral vein of the subject. With reference to FIG. 8, in one embodiment, the internal jugular vein 1502 is punctured using known techniques. A guide wire may be positioned to access the heart to facilitate insertion of the leading end 2080 of catheter 2000 within the heart through techniques known in the art. An entry opening or venotomy 1500 is made above the clavicle, through the skin and the subcutaneous tissue. The distal end 2080 of catheter 2000 is inserted through the internal jugular vein 1502, the superior vena cava 1504 and into the right atrium 1506. The positioning of the leading end 2080 of catheter 2000 may be confirmed with an x-ray if desired. The proximal trailing end 2100 of the catheter 2000 may extend from the venotomy site 1500.

Once the distal leading end 2080 of catheter 2000 is in position, attention is directed to preparing the subcutaneous tunnel incorporating the tunneling approach from the venotomy site 1500 to an exit opening 1508. Exit opening 1508 is made adjacent to the chest wall below the venotomy site 1500 to define one base of the tunnel. Thereafter, an optional dilator element may be mounted to the tunneling system 10 (FIG. 1A). Offset segment 110 (FIG. 1I) of tunneling system 10 may be introduced within the venotomy site 1500 and advanced toward the exit opening 1508. As tunneling system 10 is advanced toward the exit opening 1508, the dilator element engages internal tissue beneath the venotomy site 1500. Tunneling system 10 is then retracted toward the venotomy site 1500 and the dilator element is removed from tunneling system 10. The use of a dilator element in this procedure is disclosed in commonly assigned U.S. patent application Ser. No. 12/041,422, filed Feb. 5, 2007, the entire contents of such disclosure being incorporated herein by reference.

Figure 9:
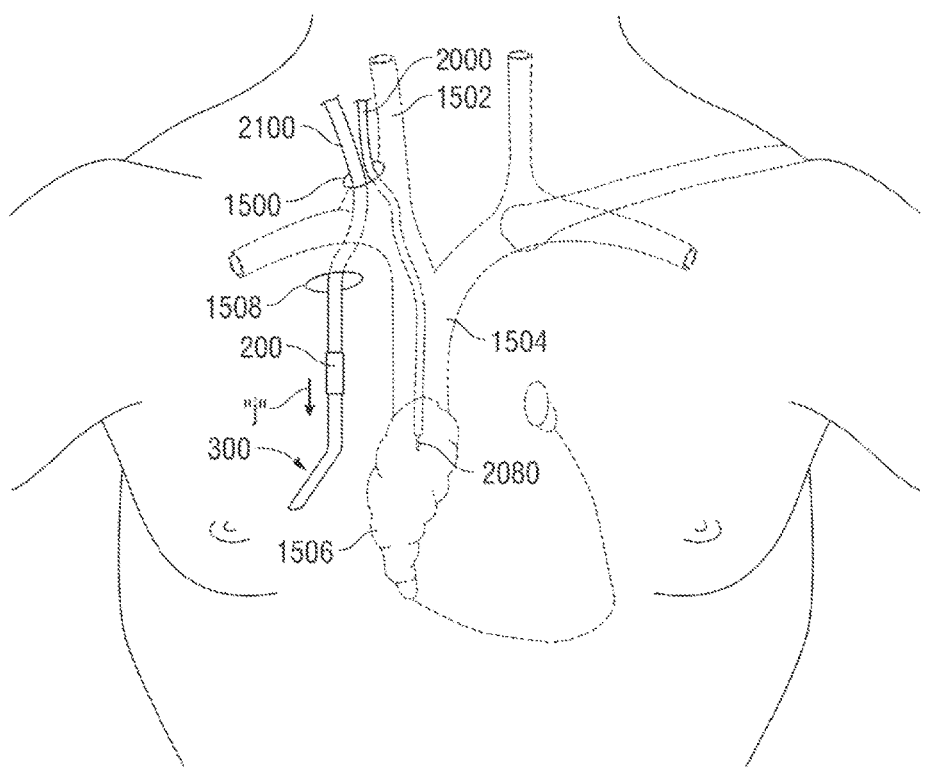

Referring now to FIG. 9, connector 200, or any of the other disclosed connector, is then connected to the catheter 2000 to secure the catheter 200 to the tunneling system 10. Flushing of catheter 2000 may be effected by distributing fluid through an internal lumen 116 (if provided) of the tunneler instrument. Once the catheter 2000 is secured, tunneling system 10 is readvanced in the direction of directional arrow "j" from the venotomy site 1500 through the exit opening 1508 until the ends of the catheter 2000 is exposed from the exit opening 1508. The relatively small profile of the connector 200 facilitates passage of the connector 200 through tissue. The catheter 2000 is removed from its mounting to tunneling system 10 and connected to a hemodialysis machine. In one embodiment, catheter 2000 is released from its mounting to connector 200 by exerting a linear force on catheter 2000. Alternatively, with a more permanent connection with connector 200, the catheter 2000 is severed or cut adjacent the connector 200 to expose the catheter ends.

Figure 10:
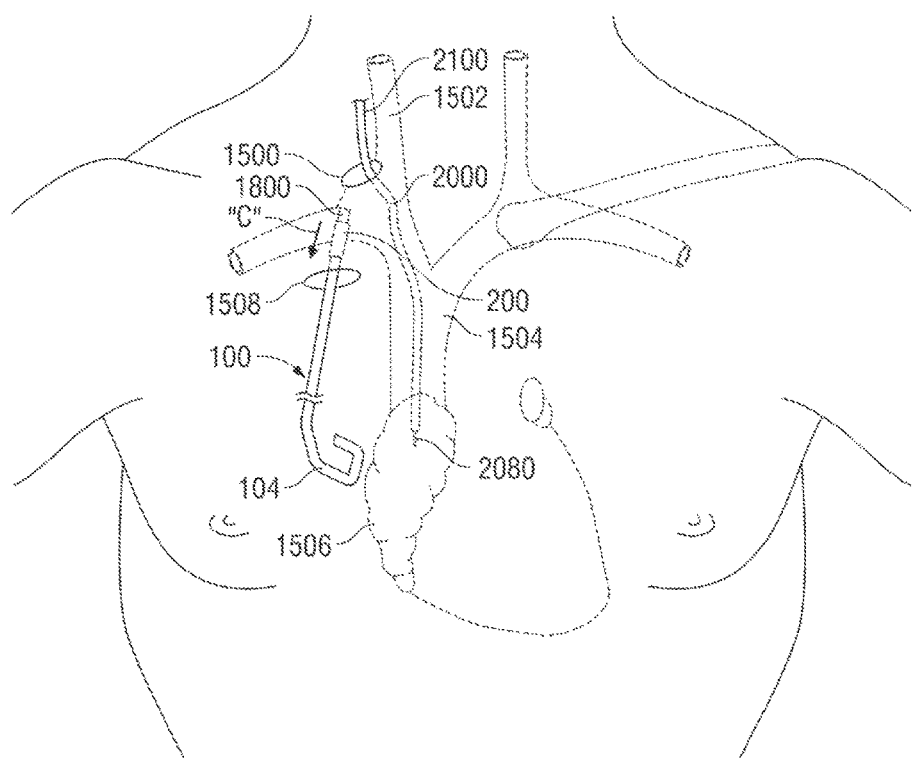
FIGS. 10-11 are views of a chest area of the subject illustrating the steps of an alternate reverse tunneling procedure.

Alternatively, the clinician may mount a cover 1800 (FIG. 10) over connector 200 and use element tunneling member 100 to tunnel or advance through the subcutaneous tunnel in accordance with, e.g., a reverse tunneling procedure for catheter insertion, as illustrated in FIG. 10. In one contemplated method, a tunnel may be made from the exit opening 1508 to the venotomy site 1500. Elongate tunneling member 100 with cover 1800 mounted thereto is introduced within the exit site 1508 and advanced toward the venotomy site 1500 (as shown schematically by arrows "C") to create or pass through a subcutaneous tunnel. Cover 1800 of elongate tunneling member 100 is designed with optimized geometry to permit effective dissection of subcutaneous tissue as it is advanced toward the venotomy site 1500. Once cover 1800 is exposed or extends from the venotomy site 1500, the cover 1800 is removed from elongate tunneling member 100.

Figure 11:
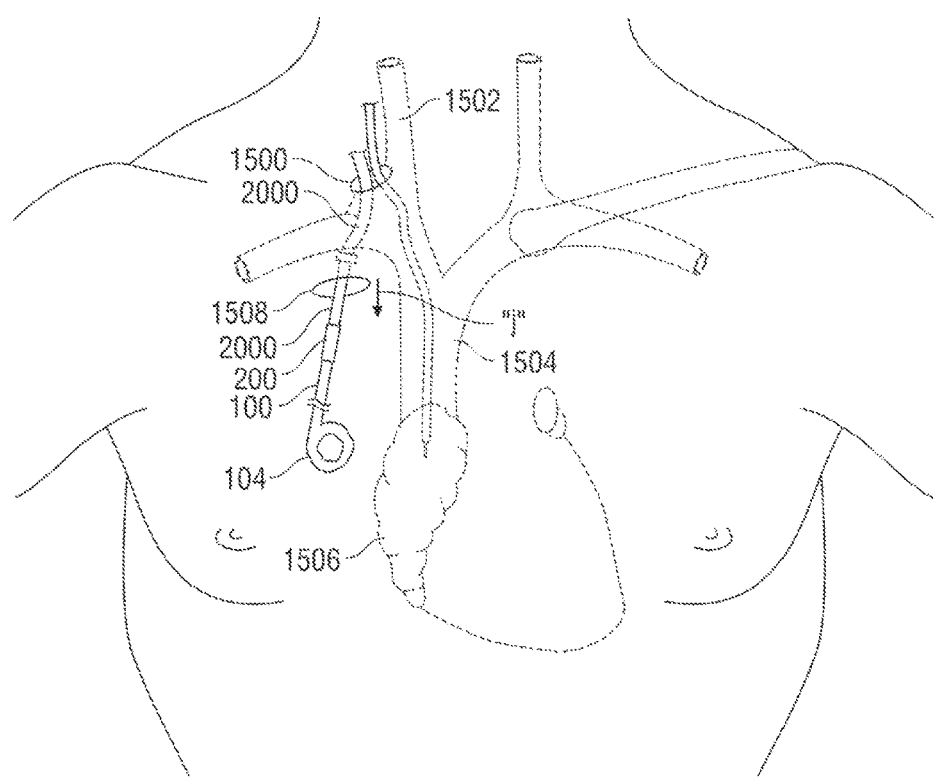

Referring now to FIG. 11, catheter 2000 is then secured to elongate tunneling member 100 through connector 200 by positioning first and second mounting elements 206, 208 of bifurcated segment 204 within the longitudinal lumens 302, 304 of the catheter 300. With the catheter 2000 attached, elongate tunneling member 100 is drawn or pulled back toward the exit site 1508 in the direction of directional arrows "j" as shown in FIG. 11. Once the proximal end of the catheter 2000 is exposed from the exit site 1508, the catheter 2000 is released from elongate tunneling member 100. The catheter 2000 may then be assembled to be connected to a hemodialysis machine.

It will be understood that various modifications may be made to the embodiments disclosed herein. Therefore, the above description should not be construed as limiting, but merely as exemplifications of the embodiments. Those skilled in the art will envision other modifications within the scope and spirit of the present disclosure.

What it claimed is:
1. A system comprising:
an elongate tunneling member defining a longitudinal axis, the elongate tunneling member defining a tunneling member lumen extending along the longitudinal axis from a port positioned at or proximate to a proximal end of the elongate tunneling member to an opening at a distal-most end of the elongate tunneling member; and a connector defining a connector lumen and including a tunneling connector segment configured to releasably couple to a distal portion of the elongate tunneling member, the distal portion comprising the distal-most end of the elongate tunneling member, and a catheter connector segment configured to couple to a catheter, the connector lumen being in fluid communication with the tunneling member lumen when the tunneling connector segment is coupled to the distal portion of the elongate tunneling member.

2. The system of claim 1, further comprising the catheter coupled to the catheter connector segment of the connector, the catheter defining a catheter lumen, wherein the connector lumen fluidically connects the tunneling member lumen and the catheter lumen when the tunneling connector segment is coupled to the distal portion of the elongate tunneling member and the catheter connector segment is coupled to the catheter.

3. The system of claim 1, wherein the proximal end of the elongate tunneling member includes a handle dimensioned for grasping engagement by a clinician.

4. The system of claim 3, wherein the port is defined in the handle.

5. The system of claim 1, wherein the port is in alignment with the longitudinal axis.

6. The system of claim 1, wherein the catheter connector segment includes a bifurcated segment including first and second mounting elements extending in a longitudinal direction, the first and second mounting elements being dimensioned for reception within respective lumens of the catheter.

7. The system of claim 6, wherein each of the first and second mounting elements has a lumen extending therethrough.

8. The system of claim 1, wherein the distal portion of the elongate tunneling member includes a threaded tip, the threaded tip being configured to be received within and engaged with the tunneling connector segment of the connector.

9. The system of claim 1, wherein the distal portion of the elongate tunneling member includes a barb extending radially away from the longitudinal axis, and wherein the tunneling connector segment defines an annular indentation configured to receive the barb.

10. The system of claim 1, wherein the distal portion of the elongate tunneling member includes a plurality of ribs extending radially away from the longitudinal axis, and wherein the tunneling connector segment defines a slot configured to receive the plurality of ribs.

11. The system of claim 1, wherein the elongate tunneling member has an outer wall defining a locking recess adjacent the distal portion, and wherein the tunneling connector segment of the connector includes a plurality of radially spaced axial ribs, each axial rib having a locking detent depending radially inwardly and configured to be received within the locking recess of the elongate tunneling member to releasably secure the connector to the elongate tunneling member.

12. The system of claim 11, wherein the axial ribs are configured to flex outwardly upon at least partial insertion of the distal portion of the elongate tunneling member within the connector to permit the locking detents to be received within the locking recess of the elongate tunneling member.

13. The system of claim 1, wherein one of the distal portion of the elongate tunneling member or the tunneling connector segment of the connector includes a ball, and wherein the other of the distal portion of the elongate tunneling member or the tunneling connector segment of the connector includes a socket adapted to receive the ball to establish a releasable coupling therebetween.

14. The system of claim 1, wherein the proximal end of the elongate tunneling member includes an offset segment obliquely arranged with respect to the longitudinal axis.

15. A system comprising:
a catheter defining a catheter lumen;
an elongate tunneling member defining a tunneling member lumen extending from a port positioned at or proximate to a proximal end of the elongate tunneling member to a distal-most end of the elongate tunneling member; and
a connector defining a connector lumen and including a tunneling connector segment configured to releasably couple to a distal portion of the elongate tunneling member, the distal portion comprising the distal-most end of the elongate tunneling member, and a catheter connector segment configured to couple to the catheter, the connector lumen fluidically connecting the catheter lumen and the elongate tunneling member lumen when the tunneling connector segment is coupled to the distal portion of the elongate tunneling member and the catheter connector segment is coupled to the catheter.

16. The system of claim 15, wherein the catheter connector segment includes a bifurcated segment including first and second mounting elements extending generally in a longitudinal direction, the first and second mounting elements being dimensioned for reception within respective lumens of the catheter, at least one of the first and second mounting elements having a lumen extending therethrough and in fluid communication with the tunneling member lumen when the connector is coupled to the elongate tunneling member.

17. The system of claim 15, wherein the proximal end of the elongate tunneling member includes a handle dimensioned for grasping engagement by a clinician, the tunneling member lumen extending along a longitudinal axis of the elongate tunneling member from a port defined in the handle to the distal portion.

18. The system of claim 15, wherein the tunneling member lumen extends along a longitudinal axis of the elongate tunneling member from the port to the distal portion, wherein the port is in alignment with the longitudinal axis.

19. The system of claim 15, the elongate tunneling member defining a longitudinal axis along a longitudinal length thereof, wherein the proximal end of the elongate tunneling member includes an offset segment obliquely arranged with respect to the longitudinal axis.

* * * * *